United States Patent
Ting et al.

(10) Patent No.: US 9,885,014 B2
(45) Date of Patent: Feb. 6, 2018

(54) RE-CONDITIONED SERUM-FREE CULTURE MEDIUM COMPOSITION OBTAINED BY CULTURING MAMMALIAN CELLS IN FIBROMODULIN

(71) Applicant: The Regents of the University of California, Oakland, CA (US)

(72) Inventors: Kang Ting, Beverly Hills, CA (US); B. Chia Soo, Beverly Hills, CA (US); Zhong Zheng, Van Nuys, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 13/677,186

(22) Filed: Nov. 14, 2012

(65) Prior Publication Data
US 2013/0078223 A1 Mar. 28, 2013

Related U.S. Application Data

(63) Continuation of application No. PCT/US2011/036216, filed on May 12, 2011.

(60) Provisional application No. 61/334,315, filed on May 13, 2010.

(51) Int. Cl.
*C12N 5/00* (2006.01)
*A61K 35/545* (2015.01)
*C12N 5/074* (2010.01)

(52) U.S. Cl.
CPC .......... *C12N 5/0018* (2013.01); *A61K 35/545* (2013.01); *C12N 5/0696* (2013.01); *C12N 2501/998* (2013.01)

(58) Field of Classification Search
CPC ................ C12N 5/0018; C12N 5/0696; C12N 2501/998; A61K 35/545
See application file for complete search history.

(56) References Cited

U.S. PATENT DOCUMENTS

| | | | |
|---|---|---|---|
| 5,614,547 A | 3/1997 | Hamilton | |
| 5,654,270 A * | 8/1997 | Ruoslahti et al. | 514/9.4 |
| 7,282,510 B2 | 10/2007 | Hamilton | |
| 2004/0142861 A1 * | 7/2004 | Mansbridge | 514/12 |
| 2006/0286668 A1 * | 12/2006 | Price | C12N 5/0043 435/325 |
| 2008/0152639 A1 | 6/2008 | Soo | |
| 2008/0233610 A1 * | 9/2008 | Thomson et al. | 435/29 |
| 2010/0330182 A1 * | 12/2010 | Young et al. | 424/484 |

FOREIGN PATENT DOCUMENTS

| | | |
|---|---|---|
| CN | 1506042 A | 6/2004 |
| WO | WO 2005/003320 | 1/2005 |
| WO | WO 2007/097494 | 8/2007 |
| WO | WO 2008/156685 | 12/2008 |
| WO | WO 2009/079007 | 6/2009 |
| WO | WO 2010033906 A2 * | 3/2010 |
| WO | WO 2011/143400 | 11/2011 |

OTHER PUBLICATIONS

Li et al. "Pluripotency can be rapidly and efficiently induced in human amniotic fluid-derived cells." Hum. Mol. Genet. (2009) 18 (22): 4340-4349.*
Zhang et al. "Characterization of differential properties of rabbit tendon stem cells and tenocytes." BMC Musculoskeletal Disorders Jan. 2010, 11 (10): pp. 1-11.*
Li et al. "Pluripotency can be rapidly and efficiently induced in human amniotic fluid-derived cells." Hum. Mol. Genet. (2009) 18 (22): pp. 4340-4349.*
Zheng et al. "Reprogramming of human fibroblasts into multipotent cells with a single ECM proteoglycan, fibromodulin." Biomaterials. Aug. 2012;33(24):5821-31.*
SIGMA Aldrich DMEM product description. accessed from http://www.sigmaaldrich.com/life-science/cell-culture/classical-media-salts/dmem.html. Aug. 6, 2015.*
Stemcell Technologies Alpha Mem product description. acessed from http://www.stemcell.com/~/media/Technical%20Resources/A/C/C/7/7/29847%20PIS.pdf?la=en. Aug. 6, 2015.*
GIBCO Serum-Free product catalog.acessed https://www.lifetechnologies.com/us/en/home/life-science/cell-culture/mammalian-cell-culture/serum-free-media.html. Aug. 6, 2015.*
Pawitan, J. "Prospect of stem cell conditioned medium in regenerative medicine."Biomed Res Int. 2014;2014:965849. pp. 1-15.*
Schulze-Tanil, "Activation and dedifferentiation of chondrocytes: Implications in cartilage injury and repair" Annals of Anatomy, vol. 191, pp. 325-338 (2009).
Goessler et al., Vergleich der genexpressions muster humaner chondrozyten und chondrogen differenzierter mesenchymaler stammzellen für das tissue-engineering, HNO, vol. 54, No. 4, pp. 258-266 (2006).
Zhong et al., "Reprogramming of human fibroblack into multiotent cells with a single ECM proteoglycan, fibromodulin" Biomaterials, Elsevier Science Publishers BV, Barking, GB, vol. 33, No. 24, pp. 5821-5831 (2012).
Steiner JP et al., "Neurotrophic immunophilin ligands stimulate structural and functional recovery in neurodegenerative animal models" Proceedings of the National Academy of Sciences of the United States, vol. 94, No. 5, pp. 2019-2024 (1997).
Written Opinion of the International Searching Authority for International App. No. PCT/US2012/036216, dated Jan. 11, 2012, 6 pages.

(Continued)

*Primary Examiner* — Titilayo Moloye
(74) *Attorney, Agent, or Firm* — Duane Morris LLP (57) ABSTRACT

The present invention provides pluripotent stem cell like (PSCL) cells or clones, a culture medium therefore, and a supernatant thereof, and methods of making and using the same.

2 Claims, 6 Drawing Sheets

(56) References Cited

OTHER PUBLICATIONS

International Preliminary Report on Patentability for International App. No. PCT/US2012/036216, dated Nov. 13, 2012, 7 pages.
International Search Report for International App. No. PCT/US2012/036216, dated Jan. 11, 2012, 5 pages.
Li, C. et al., "Pluripotency can be rapidly and efficiently induced in human amniotic fluid-derived cells", Human Molecular Genetics, vol. 18, No. 22, 2009; pp. 4340-4349.

* cited by examiner

RE-CONDITIONED SERUM-FREE CULTURE MEDIUM COMPOSITION OBTAINED BY CULTURING MAMMALIAN CELLS IN FIBROMODULIN

CROSS-REFERENCE TO RELATED APPLICATIONS

This application is a continuation application of International Application No. PCT/US2011/036216 filed on May 12, 2011, which in turn claims the benefit of U.S. Provisional Patent Application No. 61/334,315, filed May 13, 2010, the teaching of which is incorporated herein by reference in its entirety.

FIELD OF THE INVENTION

The present invention relates generally to method and composition for inducing human pluripotent stem cells.

BACKGROUND

Embryonic stem (ES) cells are pluripotent cells capable of both proliferation in cell culture and differentiation towards a variety of lineage-restricted cell populations that exhibit multipotent properties (Odorico et al., Stem Cells 19:193-204 (2001)). Because of these characteristics, ES cells, including human ES cells, can become very specific cell types that perform a variety of functions.

Generally, human ES cells are highly homogeneous, have a capacity for self-renewal and have an ability to differentiate into any functional cell in the body. Self-renewal can, under appropriate conditions, lead to a long-term proliferating capability with a potential for unlimited expansion in cell culture. In addition, if human ES cells differentiate in an undirected fashion, a heterogeneous population of cells is obtained that express markers for a plurality of different tissue types (WO 01/51616; and Shamblott et al., Proc. Natl. Acad. Sci. USA 98:113 (2001)). These features make human ES cells a unique, homogeneous, starting population for the production of cells having therapeutic utility.

Human ES cells can be used to make a variety of differentiated cells types for scientific and commercial research use. At present, differentiated human cells of many types are not readily available and cannot be expanded in significant numbers in vitro culture. Human ES cells, however, can expand indefinitely in culture and can differentiate into many, if not all, the differentiated cell types of the human body. As such, culture techniques are being developed to induce human ES cells to differentiate into any number of specific cell types of the human body. The availability of human ES cells has opened the possibility that many differentiated human cells will become available in significant numbers for scientific and commercial research.

One difficulty in working with human ES cells is the development of conditions for the standardized culture of human ES cells without the use of animal products or products such as serum, which tend to vary from batch to batch. As such, the art desires culture conditions of human ES cell culture to be as defined as possible.

To work toward that desire, a set of culture conditions was recently described that permitted the long-term culture of undifferentiated human ES cells in defined conditions. Ludwig et al., Nat. Methods 3:637-646 (2006), incorporated herein by reference as if set forth in its entirety. Ludwig et al. described a medium, referred to herein as TeSR™ medium, for cultivation of human ES cells in which each constituent of the medium was fully disclosed and characterized. TeSR™ is therefore a fully defined and sufficient medium for human ES cell culture. TeSR™ has proven effective for use in the derivation of new human ES cell lines as well, which is an even more challenging constraint than the culture of undifferentiated human ES cells.

Human ES cells preferentially remain undifferentiated when grown in environments in which the cells are in direct contact with other cells or with physical structures in their environment. In other cellular environments, human ES cells begin to differentiate and become incapable of indefinite proliferation.

This is significant in the process of cloning an ES cell culture. As used herein, "cloning" means a process of initiating an ES cell culture from a starting culture, ideally, from a single ES cell or at least from very few ES cells. Culture conditions that permit clonal culture of undifferentiated ES cells may be the most demanding conditions of all of those required in normal ES cell culture and proliferation.

In spite of the progress in effectively culturing ES cells, several significant disadvantages with these methods still exist. For example, exposure to animal pathogens through MEF-conditioned medium or matrigel matrix is still a possibility. The major obstacle of the use of human ES cells in human therapy is that the originally described methods to propagate human ES cells involve culturing the human ES cells on a layer of feeder cells of non-human origin, and in the presence of nutrient serum of non-human origin. More recently, extensive research into improving culture systems for human ES cells has concentrated on the ability to grow ES cells under serum free/feeder-free conditions. For example, to ensure a feeder-free environment for the growth of human ES cells, a substitute system based on medium supplemented with serum replacement (SR), transforming growth factor .beta.1 (TGF-.beta.1), LIF, bFGF and a fibronectin matrix has also been tried (Amit et al (2004), Biol. Reprod. 70(3):837-45). Evaluation of methods for derivation and propagation of undifferentiated human ES cells on human feeders or feeder-free matrices continues.

SUMMARY OF THE INVENTION

The present invention provides a method and composition for reprogramming a cell into a pluripotent stem cell like (PSCL) cell or clone, a culture medium for the method of invention, a PSCL cell or clone, and a method using the PSCL cell or clone to treat or ameliorate a disorder.

In one aspect, the present invention provides a cell culture medium composition comprising fibromodulin (FMOD) or a derivative or fragment thereof, wherein the composition is effective for reprogramming a cell so as to form a pluripotent stem cell like (PSCL) clone, wherein the PSCL clone is recognized by an antibody against human Oct4A, Sox2, Nanog, SSEA4, TRA-1-60(S), or TRA-1-181 in immunofluorescent staining In some embodiments, the FMOD is a FMOD protein or peptide. The cell culture medium composition can have FMOD protein or peptide in various concentrations. In some embodiments, the composition has FMOD in a concentration from about 200 nM to about 800 nM.

In the above composition, the cell can be any mammalian cell. In some embodiments, the cell is a human cell, mouse cell, or rat cell. Examples of human cells include, e.g., BJ, MRC-5 and NHDF.

In another aspect, the present invention provides a method to reprogram a mammalian cell into a PSCL cell or clone. In some embodiments, the method comprises:

treating a mammalian cell with a cell culture medium for a period ranging from a day to a month, and changing the cell culture medium regularly until a pluripotent stem cell like (PSCL) clone forms;

wherein the medium comprises fibromodulin (FMOD) or a derivative or fragment thereof, wherein the composition is effective for reprogramming the cell so as to form the PSCL clone, and wherein the PSCL clone is recognized by an antibody against human Oct4A, Sox2, Nanog, SSEA4, TRA-1-60(S), or TRA-1-181 in immunofluorescent staining In some embodiments, the FMOD is a FMOD protein or peptide.

In the above method, the cell culture medium composition can have FMOD protein or peptide in various concentrations. In some embodiments, the composition has FMOD in a concentration from about 200 nM to about 800 nM.

In the above method, the cell can be any mammalian cell. In some embodiments, the cell is a human cell, mouse cell, or rat cell. Examples of human cells include, e.g., BJ, MRC-5NHDF, keratinocytes, melanocytes, peripheral blood cells (e.g., CD34+), cord blood cells or even certain stem cells (e.g., adipose-derived stem cells, perivascular stem cells, or neural stem cells).

In a further aspect of the present invention, it is provided a pluripotent stem cell like (PSCL) cell or clone, generated by a method comprising:

treating a mammalian cell with a cell culture medium for a period ranging from a day to a month, and changing the cell culture medium regularly until the PSCL clone forms;

wherein the medium comprises fibromodulin (FMOD) or a derivative or fragment thereof, wherein the composition is effective for reprogramming the cell so as to form the PSCL clone, and wherein the PSCL clone is recognized by an antibody against human Oct4A, Sox2, Nanog, SSEA4, TRA-1-60(S), or TRA-1-181 in immunofluorescent staining In some embodiments, the FMOD is a FMOD protein or peptide.

In the above method, the cell culture medium composition can have FMOD protein or peptide in various concentrations. In some embodiments, the composition has FMOD in a concentration from about 200 nM to about 800 nM.

In the above method, the cell can be any mammalian cell. In some embodiments, the cell is a human cell, mouse cell, or rat cell. Examples of human cells include, e.g., BJ, MRC-5, NHDF, keratinocytes, melanocytes, peripheral blood cells (e.g., CD34+), cord blood cells or even certain stem cells (e.g., adipose-derived stem cells, perivascular stem cells, neural stem cells). The PSCL cell or clone can be used to treat or ameliorate any disorder that can be treated or ameliorated by a pluripotent or totipotent stem cell. Generally, the method comprises administering to a mammalian subject (e.g., a human being or an animal) a PSCL cell or clone disclosed herein. In some embodiments, the disorder can be a neurodegenerative disorder.

In some embodiments, the disorder can be a central nervous system (CNS) disease, cardiovascular disease, blood diseases, Crohn's disease, bone disease, muscle disease, or chondrocyte disease.

In some embodiments, the disorder can be a retina disease.

In some embodiments, the disorder can be a trauma and injury to a tissue. Examples of such tissue can be skin, muscle, cartilage, tendon, peripheral nerve, spinal cord, blood vessels, or bone.

In some embodiments, the disorder can be a skeletal disorder.

In some embodiments, the disorder can be an organ disease.

In another aspect, it is provided a supernatant comprising a culture medium disclosed herein, embodiments of which are described above and below. The supernatant is effective for treating or ameliorating a disorder as is the PSCL cell or clone disclosed herein. In some embodiments, the present invention provides a composition comprising a supernatant disclosed herein. The composition can be a pharmaceutical or cosmetic composition, which can be administered to a mammalian subject to treat or ameliorate a disorder disclosed herein.

DETAILED DESCRIPTION OF EXEMPLARY EMBODIMENTS

In one aspect, the present invention provides a method for reprogramming a mammalian cell into a pluripotent stem cell like (PSCL) cell. The method generally comprises treating a mammalian cell with a culture medium for a sufficient period of time to cause the mammalian cell to be reprogrammed into a cell or clone that exhibits or possess one or more characteristics or properties of a pluripotent stem cell. In some embodiments, the culture medium comprises a fibromodulin (FMOD) protein or peptide, or a derivative or fragment thereof.

In some embodiments, the culture medium can include a FMOD protein or peptide in a concentration from about 1 nM to about 1000 µM, e.g., from about 1 nM to about 10 nM, from about 1 nM to about 20 nM, from about 1 nM to about 50 nM, from about 1 nM to about 100 nM, from about 1 nM to about 200 nM, from about 1 nM to about 500 nM, from about 1 nM to about 1000 nM, from about 1 nM to about 2 µM, from about 1 nM to about 5 µM, from about 1 nM to about 10 µM, from about 1 nM to about 20 µM, from about 1 nM to about 50 µM, from about 1 nM to about 100 µM, from about 1 nM to about 200 µM, or from about 1 nM to about 500 µM.

In some embodiments, the culture medium can include a FMOD protein or peptide in a concentration from about 10 nM to about 1000 µM, e.g., from about 10 nM to about 20 nM, from about 10 nM to about 50 nM, from about 10 nM to about 100 nM, from about 10 nM to about 200 nM, from about 10 nM to about 500 nM, from about 10 nM to about 1000 nM, from about 10 nM to about 2 µM, from about 10 nM to about 5 µM, from about 10 nM to about 10 µM, from about 10 nM to about 20 µM, from about 10 nM to about 50 µM, from about 10 nM to about 100 µM, from about 10 nM to about 200 µM, or from about 10 nM to about 500 µM.

In some embodiments, the culture medium can include a FMOD protein or peptide in a concentration from about 20 nM to about 1000 µM, e.g., from about 20 nM to about 50 nM, from about 20 nM to about 100 nM, from about 20 nM to about 200 nM, from about 20 nM to about 500 nM, from about 20 nM to about 1000 nM, from about 20 nM to about 2 µM, from about 20 nM to about 5 µM, from about 20 nM to about 10 µM, from about 20 nM to about 20 µM, from about 20 nM to about 50 µM, from about 20 nM to about 100 µM, from about 20 nM to about 200 µM, or from about 20 nM to about 500 µM.

In some embodiments, the culture medium can include a FMOD protein or peptide in a concentration from about 50 nM to about 1000 µM, e.g., from about 50 nM to about 100 nM, from about 50 nM to about 200 nM, from about 50 nM to about 500 nM, from about 50 nM to about 1000 nM, from about 50 nM to about 2 µM, from about 50 nM to about 5 µM, from about 50 nM to about 10 µM, from about 50 nM to about 20 µM, from about 50 nM to about 50 µM, from about 50 nM to about 100 µM, from about 50 nM to about 200 µM, or from about 50 nM to about 500 µM.

In some embodiments, the culture medium can include a FMOD protein or peptide in a concentration from about 100 nM to about 1000 µM, e.g., from about 100 nM to about 200 nM, from about 100 nM to about 500 nM, from about 100 nM to about 1000 nM, from about 100 nM to about 2 µM, from about 100 nM to about 5 µM, from about 100 nM to about 10 µM, from about 100 nM to about 20 µM, from about 100 nM to about 50 µM, from about 100 nM to about 100 µM, from about 100 nM to about 200 µM, or from about 100 nM to about 500 µM.

In some embodiments, the culture medium can include a FMOD protein or peptide in a concentration from about 200 nM to about 1000 µM, e.g., from about 200 nM to about 500 nM, from about 200 nM to about 1000 nM, from about 200 nM to about 2 µM, from about 200 nM to about 5 µM, from about 200 nM to about 10 µM, from about 200 nM to about 20 µM, from about 200 nM to about 50 µM, from about 200 nM to about 100 µM, from about 200 nM to about 200 µM, or from about 200 nM to about 500 µM.

In some embodiments, the culture medium can include a FMOD protein or peptide in a concentration from about 500 nM to about 1000 µM, e.g., from about 500 nM to about 1000 nM, from about 500 nM to about 2 µM, from about 500 nM to about 5 µM, from about 500 nM to about 10 µM, from about 500 nM to about 20 µM, from about 500 nM to about 50 µM, from about 500 nM to about 100 µM, from about 500 nM to about 200 µM, or from about 500 nM to about 500 µM.

In some embodiments, the culture medium can include a FMOD protein or peptide in a concentration from about 1000 nM to about 1000 µM, e.g., from about 1000 nM to about 2 µM, from about 1000 nM to about 5 µM, from about 1000 nM to about 10 µM, from about 1000 nM to about 20 µM, from about 1000 nM to about 50 µM, from about 1000 nM to about 100 µM, from about 1000 nM to about 200 µM, or from about 1000 nM to about 500 µM.

In some embodiments, the culture medium can include a FMOD protein or peptide in a concentration from about 2 µM to about 1000 µM, e.g., from about 2 µM to about 5 µM, from about 2 µM to about 10 µM, from about 2 µM to about 20 µM, from about 2 µM to about 50 µM, from about 2 µM to about 100 µM, from about 2 µM to about 200 µM, or from about 2 µM to about 500 µM.

In some embodiments, the culture medium can include a FMOD protein or peptide in a concentration from about 5 µM to about 1000 µM, e.g., from about 5 µM to about 10 µM, from about 5 µM to about 20 µM, from about 5 µM to about 50 µM, from about 5 µM to about 100 µM, from about 5 µM to about 200 µM, or from about 5 µM to about 500 µM.

In some embodiments, the culture medium can include a FMOD protein or peptide in a concentration from about 10 µM to about 1000 µM, e.g., from about 10 µM to about 20 µM, from about 10 µM to about 50 µM, from about 10 µM to about 100 µM, from about 10 µM to about 200 µM, or from about 10 µM to about 500 µM.

In some embodiments, the culture medium can include a FMOD protein or peptide in a concentration from about 20 µM to about 1000 µM, e.g., from about 20 µM to about 50 µM, from about 20 µM to about 100 µM, from about 20 µM to about 200 µM, or from about 20 µM to about 500 µM.

In some embodiments, the culture medium can include a FMOD protein or peptide in a concentration from about 50 µM to about 1000 µM, e.g., from about 50 µM to about 100 µM, from about 50 µM to about 200 µM, or from about 50 µM to about 500 µM.

In some embodiments, the culture medium can include a FMOD protein or peptide in a concentration from about 100 µM to about 1000 µM, e.g., from about 100 µM to about 200 µM, or from about 100 µM to about 500 µM.

In some embodiments, the culture medium can include a FMOD protein or peptide in a concentration from about 500 µM to about 1000 µM.

In addition to the FMOD protein or peptide or a derivative or fragment thereof, the culture medium can be any cell culture medium commonly used in the art. For example, the culture medium generally includes saline. An example of cell culture medium includes, e.g., saline, a pH of 7.4 PBS, DMEM medium, or fibroblast basic medium (FBM, Lonza). In some embodiments, the culture medium can include additional components or agents, e.g., transforming growth factor (TGF)-β.

Examples of the concentration of FMOD protein or peptide in the culture medium can be, e.g., about 10 nM, about 20 nM, about 50 nM, about 100 nM, about 200 nM (e.g., 220 nM), about 500 nM, about 1000 nM, about 2 µM, about 5 µM, about 10 µM, about 20 µM, about 50 µM, about 100 µM, about 200 µM, or about 500 µM.

As used herein, the term "sufficient time" shall mean a period sufficiently long to reprogram the mammalian cell by the culture medium disclosed herein. In some embodiments, the term "sufficient time" ranges from hours to about 180 days, e.g., from 8 hrs to about 12 hrs, from about 8 hrs to about 24 hrs, from about 8 hrs to about 2 days, from about 8 hrs to about 7 days, from about 8 hrs to about 14 days, from about 8 hrs to about 21 days, from about 8 hrs to about 30 days, from about 8 hrs to about 45 days, from about 8 hrs to about 60 days, from about 8 hrs to about 90 days, from about 8 hrs to about 120 days, from about 8 hrs to about 150 days, or from about 8 hrs to about 180 days.

In some embodiments, the term "sufficient time" ranges from 1 day to about 180 days, e.g., from about 1 day to about 2 days, from about 1 day to about 7 days, from about 1 day to about 14 days, from about 1 day to about 21 days, from about 1 day to about 30 days, from about 1 day to about 45 days, from about 1 day to about 60 days, from about 1 day to about 90 days, from about 1 day to about 120 days, from about 1 day to about 150 days, or from about 1 day to about 180 days.

In some embodiments, the term "sufficient time" ranges from 2 days to about 180 days, e.g., from about 2 days to about 7 days, from about 2 days to about 14 days, from about 2 days to about 21 days, from about 2 days to about 30 days, from about 2 days to about 45 days, from about 2 days to about 60 days, from about 2 days to about 90 days, from about 2 days to about 120 days, from about 2 days to about 150 days, or from about 2 days to about 180 days.

In some embodiments, the term "sufficient time" ranges from 7 days to about 180 days, e.g., from about 7 days to about 14 days, from about 7 days to about 21 days, from about 7 days to about 30 days, from about 7 days to about 45 days, from about 7 days to about 60 days, from about 7 days to about 90 days, from about 7 days to about 120 days, from about 7 days to about 150 days, or from about 7 days to about 180 days.

In some embodiments, the term "sufficient time" ranges from 14 days to about 180 days, e.g., from about 14 days to about 21 days, from about 14 days to about 30 days, from about 14 days to about 45 days, from about 14 days to about 60 days, from about 14 days to about 90 days, from about 14 days to about 120 days, from about 14 days to about 150 days, or from about 14 days to about 180 days.

In some embodiments, the term "sufficient time" ranges from 21 days to about 180 days, e.g., from about 21 days to about 30 days, from about 21 days to about 45 days, from about 21days to about 60 days, from about 21 days to about 90 days, from about 21 days to about 120 days, from about 21 days to about 150 days, or from about 21 days to about 180 days.

In some embodiments, the term "sufficient time" ranges from 30 days to about 180 days, e.g., from about 30 days to about 45 days, from about 30 days to about 60 days, from about 30 days to about 90 days, from about 30 days to about 120 days, from about 30 days to about 150 days, or from about 30 days to about 180 days.

In some embodiments, the term "sufficient time" ranges from 45 days to about 180 days, e.g., from about 45 days to about 60 days, from about 45 days to about 90 days, from about 45 days to about 120 days, from about 45 days to about 150 days, or from about 45 days to about 180 days.

In some embodiments, the term "sufficient time" ranges from 60 days to about 180 days, e.g., from about 60 days to about 90 days, from about 60 days to about 120 days, from about 60 days to about 150 days, or from about 60 days to about 180 days.

In some embodiments, the term "sufficient time" ranges from 90 days to about 180 days, e.g., from about 90 days to about 120 days, from about 90 days to about 150 days, or from about 90 days to about 180 days.

In some embodiments, the term "sufficient time" ranges from 120 days to about 180 days, e.g., from about 12 days to about 150 days, or from about 60 days to about 180 days.

In some embodiments, the method provided herein further includes changing culture medium with fresh culture medium regularly. The term "regularly" shall mean changing culture medium hourly, bi-hourly, four times a day, twice a day, daily, once per two-day, bi-weekly, weekly, bi-monthly, or monthly.

In another aspect of the present invention, it is provided a supernatant of the PSCL cell or clone disclosed herein. The supernatant includes the culture medium of the present invention and also growth factors and/or transcriptional factors excreted by the PSCL cells or clones provided herein. The supernatant disclosed herein is effective for treating or ameliorating a disorder as is the PSCL cell or clone disclosed herein. In some embodiments, the supernatant can form a composition, optionally with a carrier. The composition can be applied to a mammalian subject for treating or ameliorating a disorder. In some embodiments, the composition can be a cosmetic composition or a pharmaceutical composition.

Pluripotent Stem Cell Like Cell or Clone

As used herein, the term PSCL cell or clone shall mean a cell that is not a pluripotent stem cell but possesses at least one of the characteristics of PSC. The PSCL cell or clone disclosed herein has ability to differentiate into a desired tissue cell in a physiological condition of a tissue.

The characteristics or attributes of PSC are generally known in the art, some features of which are described as follows. Generally recognized characteristics of PSC include its ability to differentiate into different tissue cells under proper conditions. Other attributes of a PSC include, e.g., expression of transcriptional regulators such as Oct-4, Sox2, or Nanog or antigens such as SSEA-4, TRA-1-60, or TRA-1-81, as well as high expression of alkaline phosphatase (ALP).

In some embodiments, the PSCL cell or clone disclosed herein has all the attributes or a pluripotent stem cell. In these embodiments, the PSCL cell or clone is presumably a PSC.

In some embodiments, the PSCL cell or clone disclosed herein has one or more, but not all, of the attributes or a pluripotent stem cell. In these embodiments, the PSCL cell or clone disclosed herein does not amount to a PSC.

These transcriptional regulators or antigens can be readily recognized by antibodies against these regulators or antigens in, e.g., immunofluorescent staining As used herein, the term PSC shall also encompass pluripotent germ cells.

Method of Use

The PSCL cell or clone can be used in medicine as is a PSC to treat or ameliorate a disorder in a mammal (e.g., a human being or an animal). Generally, the method includes administering to a subject having a disorder a PSCL cell(s) or clone(s) so as to treat or ameliorate the disorder. Methods of using pluripotent stem cell to treat a disorder is generally established and known in the art as it will closely resemble the protocols used for embryonic stem cells (see, e.g., Sun, et al., Cell Cycle 9:5, 880-885 (2010)). Although, there are no approved products yet, there are a lot of potential applications, such as transplantation, gene repair and cell replacement therapy for a variety of genetic disorders (see, e.g., Gunaseelie, et al., Curr Med Chem.; 17(8): 759-766 (2010)).

The disorder can be any disorder that can be treated or ameliorated by a pluripotent stem cell. In some embodiments, the disorder can be a degenerative disease such as a neurodegenerative disorder or cardiac degenerative disease.

In some embodiments, the disorder can be a central nervous system (CNS) disease, cardiovascular disease, blood diseases, Crohn's disease, bone disease, muscle disease, baldness, cancer, infertility, or chondrocyte disease, such as adenosine deaminase deficiency-related severe combined immunodeficiency (ADA-SCID), Shwachman-Bodian-Diamond syndrome (SBDS), Gaucher disease (GD) type III, Duchenne (DMD) and Becher muscular dystrophy (BMD), Parkinson disease (PD), Huntington disease (HD), juvenile-onset, type 1 diabetes mellitus (JDM), Down syndrome (DS)/trisomy 21, the carrier state of Lesch-Nyhan syndroms, Alzheimer's disease, or ischemic heart diseases (see, e.g., Gunaseelie, et al., Curr Med Chem.; 17(8): 759-766(2010)).

In some embodiments, the disorder can be a retina disease.

In some embodiments, the disorder can be a trauma and injury to a tissue. Examples of such tissue can be skin, muscle, cartilage, tendon, peripheral nerve, spinal cord, blood vessels, or bone. Examples of trauma can be trauma inflicted by physical impact or trauma by a procedure in medicine, e.g., removal of tissue in treating cancer, etc.

In some embodiments, the disorder can be a skeletal disorder.

In some embodiments, the disorder can be an organ disease.

EXAMPLES

The following examples illustrate, rather than limit, embodiments of the present invention.
Studies on Induction of iPS Cells After Exposure to a Protein Agent and its Peptide Derivatives (Examples 1-15)
Introduction Direct reprogramming of somatic cells provides an opportunity to generate patient- or disease-specific pluripotent stem cells. Recently, pioneering work by Yamanaka and colleagues identified key transcription factors that, when overexpressed, enable reprogramming of a somatic cells to a pluripotent state (Takahashi, K. & Yamanaka, S. Cell 126, 663-676 (2006)). It is now possible to reprogram mouse and human somatic cells to induced pluripotent stem (iPS) cells by ectopic expression of the factors OCT4, SOX2, KLF4 and c-MYC or a different set of for factors (OCT4, SOX2, NANOG and LIN-28) (Okita, K., et al., Nature 448, 313-317 (2007); Takahashi, K., et al., Nat Protoc 2, 3081-3089 (2007); Maherali, N., et al. Cell Stem Cell 1, 55-70 (2007); Wernig, M., et al., Nature 448, 318-324 (2007); Yu, J., et al., Science 318, 1917-1920 (2007); Park, I. H., et al., Nature 451, 141-146 (2008); and Lowry, W. E., et al., Proc Natl Acad Sci USA 105, 2883-2888 (2008). Human iPS cell closely resemble embryonic stem (ES) cells in gene expression, pluripotency and epigenetic states, and hold great potential for regenerative medicine and in vitro disease modeling. However, the integration of vial transgenes into the somatic genome, especially oncogenes such as c-MYC and KLF, limits the utility of iPS cells. Indeed, reactivation of the c-Myc retrovirus contributes to tumor formation in chimeric mice derived from iPS cells (Okita, K., et al., Nature 448, 313-317 (2007); and Nakagawa, M., et al., Nat Biotechnol 26, 101-106 (2008)). Through optimization of the reprogramming method, it is now possible to reprogram both mouse and human somatic cells with some small-molecule chemicals replacing some of the transcription factors (Nakagawa, M., et al., Nat Biotechnol 26, 101-106 (2008); Lowry, W. E. & Plath, K., Nat Biotechnol 26, 1246-1248 (2008); Huangfu, D., et al., Nat Biotechnol 26, 1269-1275 (2008); Huangfu, D., et al., Nat Biotechnol 26, 795-797 (2008); and Maherali, N., et al., Cell Stem Cell 3, 340-345 (2008)). However, at least some of the transcription factors, such as OCT4, have to been integrated (Nakagawa, M., et al., Nat Biotechnol 26, 101-106 (2008); Lowry, W. E. & Plath, K., Nat Biotechnol 26, 1246-1248 (2008); Huangfu, D., et al., Nat Biotechnol 26, 1269-1275 (2008); Huangfu, D., et al., Nat Biotechnol 26, 795-797 (2008); and Maherali, N., et al., Cell Stem Cell 3, 340-345 (2008)). Thus, the safety issue still remains for the iPS application. In addition, transgenes process invokes huge amount of selection of identify and characterize iPS each approach (Takahashi, K. & Yamanaka, S., Cell 126, 663-676 (2006); Lowry, W. E. & Plath, K., Nat Biotechnol 26, 1246-1248 (2008); Huangfu, D., et al., Nat Biotechnol 26, 1269-1275 (2008); Huangfu, D., et al., Nat Biotechnol 26, 795-797 (2008); Maherali, N., et al., Cell Stem Cell 3, 340-345 (2008); and Takahashi, K., et al., Cell 131, 861-872 (2007)), which is extremely time consuming. For clinical practice, a new method for iPS generation, which is safer and of more efficiency, is established in the following examples.

Fibromodulin (FMOD) is a member of small leucine rich proteoglycan (SLRP). FMOD is a cytosolic secreted protein with an expression pattern restricted mainly to connective tissue and tissues rich in collagen, such as cartilage, bone, tendon and skin (Heinrich, W., et al., FEBS Lett 16, 63-67 (1971); and Heinegard, D., et al., Pathol Immunopathol Res 1988;7(1-2):27-31 7, 27-31 (1988)). Fibromodulin is involved in fibrillogenesis, cell adhesion, and cytokine activity modulation (Hildebrand, A., et al., Biochem J 302, 527-534 (1994); Zheng, Z., et al., Wound Repair and Regeneration 16, A28-A28 (2008); Zheng, Z., et al., J Am Coll Surgeons 211, S127-S127 (2010); and Zheng, Z., et al., Journal of Investigative Dermatology 131, 769-778 (2011)). Previous studies have shown that FMOD can combine with both transforming growth factor (TGF)-β isoforms and collagens to modulate signal transduction and extracellular matrix distribution (Hildebrand, A., et al., Biochem J 302, 527-534 (1994); Zheng, Z., et al., Wound Repair and Regeneration 16, A28-A28 (2008); Zheng, Z., et al., J Am Coll Surgeons 211, S127-S127 (2010); Hedbom, E. & Heinegard, D., J Biol Chem 1989 Apr 25;264(12):6898-905 264, 6898-6905 (1989); and Kalamajski, S. & Oldberg, A., Journal of Biological Chemistry 282, 26740-26745 (2007)).

Recently, FMOD was found to be a critical component of niche environment for multipotential stem cell (Bi, Y., et al., Nat Med 13, 1219-1227 (2007)). Interestingly, we found rat fibroblast cell line Rat-2 formed clones with an ES cell morphology after exposure to FMOD (Example 1, FIG. 1), which indicated that FMOD has the potential for inducing iPS cells.

Example 1

Figures 1A, 1B:
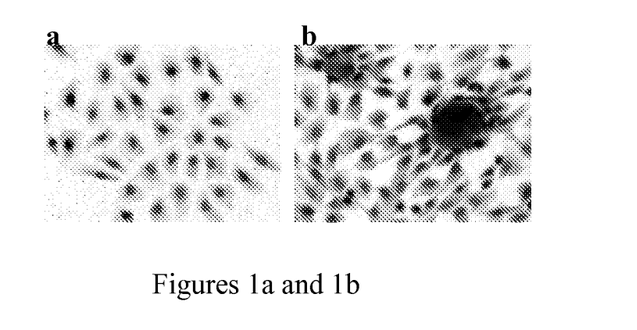
FIGS. 1a and 1b show rat-2 fibroblasts formed clones with an embryonic stem (ES) cell morphology after exposure to FMOD.

In this example, rat-2 fibroblasts formed clones with an embryonic stem (ES) cell morphology after exposure to FMOD. FIG. 1a shows Rat-2 without FMOD-treatment, and FIG. 1b shows the result of rat-2 exposed with 200 nM FMOD for 1 week.

Examples 2-3

In Examples 2-3, three human cells, including human newborn foreskin dermal fibroblast BJ cells (ATCC, CRL-2522), human fetal lung fibroblast MRC-5 cells (ATCC, CCL-171), and normal human adult dermal fibroblast NHDF cells (Lonza Group Ltd.), were used to verify this phenomenon. After exposure to FMOD for 3 to 4 weeks, all three cells could form ES-like clones (FIGS. 2-3).

Figures 2A, 2B, 2C:
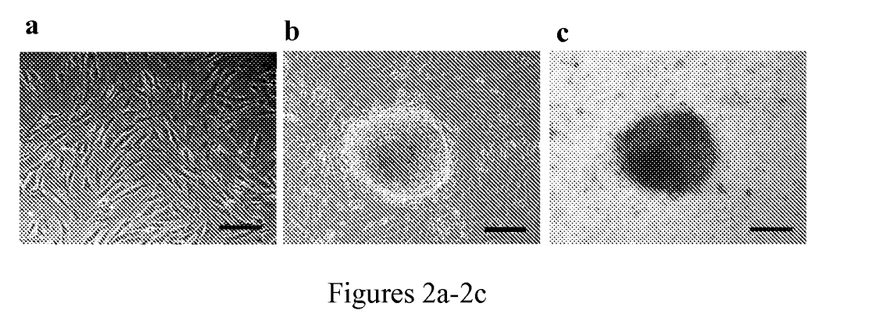
FIGS. 2a-2c show test results on human newborn foreskin dermal fibroblast BJ cells.

FIGS. 2a-2c show the results of experiments where human newborn foreskin dermal fibroblast BJ cells (a) were seeded in 24-well plates, and treated with 200 nM FMOD w/o serum for 3 weeks before transfer on feeder cells (mouse embroyinc fibroblasts treated with 6,000 rads of gamma irradiation, GlobalStem). Medium changed daily. ES-like clones were observed (b), with alkanline phosphatase (AP) staining (c) for iPS characterization. 6-8 clones were formed per 20,000 initial seeded BJ cells. Bar: 200 µ.

Figures 3A, 3B:
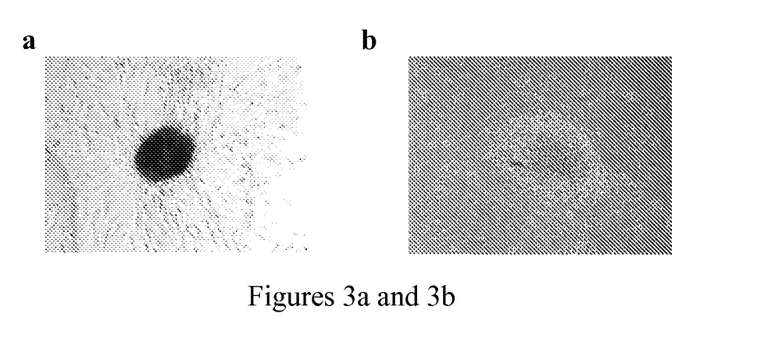
FIGS. 3a and 3b show test results on human fetal lung fibroblast MRC-5 cells.

FIGS. 3a and 3b show the results of experiments where human fetal lung fibroblast MRC-5 cells (a) and human normal adult dermal fibroblast NHDF cells (b) were seeded in 24-well plates, and treated with 200 nM FMOD without serum for 4 weeks before transfer on feeder cells. Medium changed daily. ES-like clones were observed (b) 4-10 clones were formed per 50,000 initial seeded BJ cells.

Example 4

For further confirmation, BJ cells were pre-transfected with lentivirus containing genes encoding for enhanced green fluorescent protein (EGFP) coupled with Nanog promoter [BJ (Nanog-EGFP) cells] before exposure to FMOD. After 3 weeks FMOD-treatment, BJ (Nanog-EGFP) cells also formed ES like clones with EGFP expression (FIG. 4), which indicated that Nanog gene was strongly expressed in these FMOD induced iPS (FiPS) cells, just like other iPS induced by ectopic expression of Yamanaka or Thomson factors (Takahashi, K. & Yamanaka, S., Cell 126, 663-676 (2006); Yu, J., et al., Science 318, 1917-1920 (2007); and Takahashi, K., et al., Cell 131, 861-872 (2007)).

Figure 4:
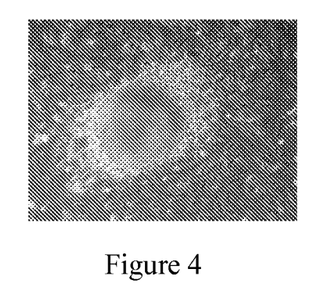
FIG. 4 shows results of tests on human newborn foreskin dermal fibroblast BJ cells.

FIG. 4 shows the results of experiments where human newborn foreskin dermal fibroblast BJ cells were pre-transfected with lentivirus containing genes encoding for EGFP coupled with Nanog promoter before exposure to 200 nM FMOD w/o serum for 3 weeks. Medium changed daily before transfer on feeder cells. ES-like clones were observed with EGFP expression.

Examples 5 and 6

Figure 5:
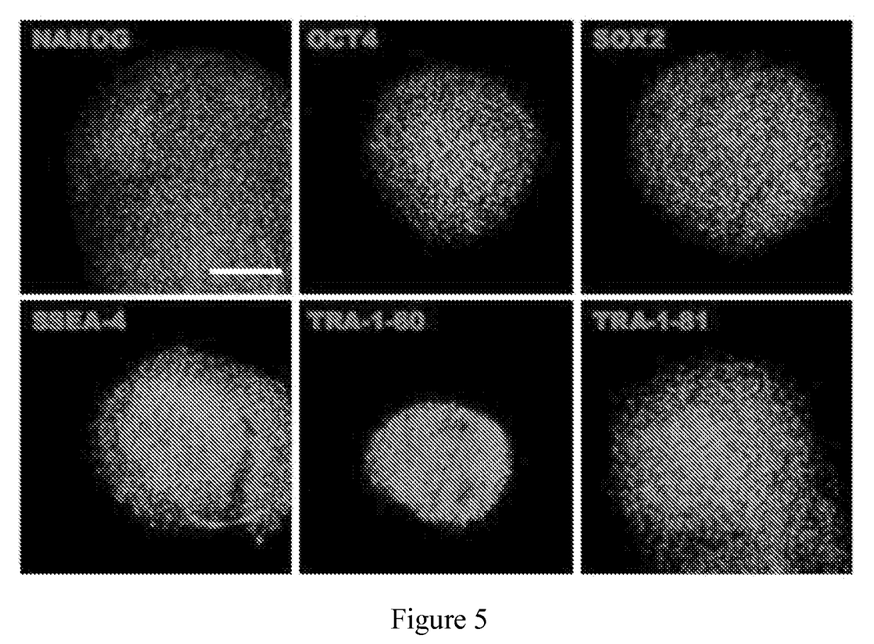
FIG. 5 shows that BJ-FiPS cells were further recognized by immunofluorescent staining with antibodies against key transcriptional regulators (NANOG, OCT4 SOX2) of human iPS cells as well as antigens expressed on the cell surface of all human pluripotent cells (SSEA4, TRA-1-60 and TRA-1-81). Bar: 200 μm.

FiPS cells induced from BJ cells (BJ-FiPS) were further recognized with antibodies against key transcriptional regulators (NANOG, OCT4 SOX2) of human iPS cells as well as antigens expressed on the cell surface of all human pluripotent cells (SSEA4, TRA-1-60 and TRA-1-81) by immunofluorescent staining (FIG. 5). RT-PCR targeted key iPS marakers (NANOG, OCT4, SOX2 and hTERT) of human iPS cells were also performed as the second evidence (FIG. 6).

FIG. 5 shows BJ-FiPS cells were further recognized by immunofluorescent staining with antibodies against key transcriptional regulators (NANOG, OCT4 SOX2) of human iPS cells as well as antigens expressed on the cell surface of all human pluripotent cells (SSEA4, TRA-1-60 and TRA-1-81). Bar: 200 µm.

Figure 6:
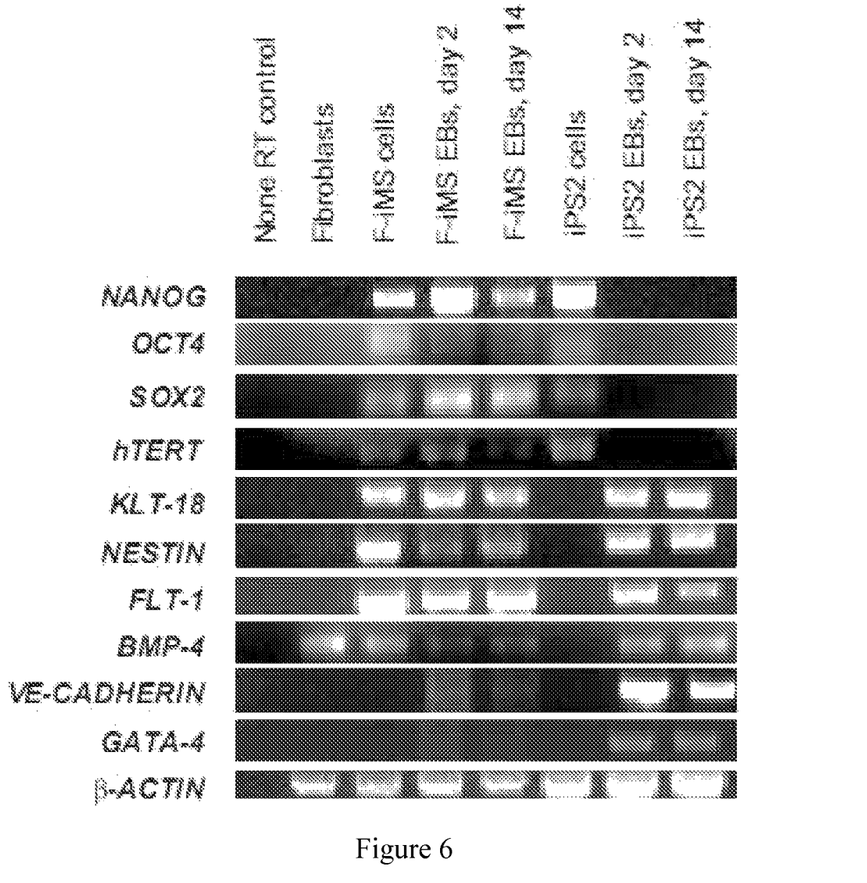
FIG. 6 shows BJ-FiPS cells were further recognized by RT-PCR. Untreated BJ cells were used as control. Primers for iPS characterization (50X2, OCT4, NANOG and hTERT), ectodermic marker (KRT-18 and NESTIN), endodermic markers (AFP and GATA-4), mesodermic marker (FLT-1, BMP-4 and VE-Cadherin) were used with control primer for β-actin.

FIG. 6 shows BJ-FiPS cells were further recognized by RT-PCR. Untreated BJ cells were used as control. Primers for iPS characterization (SOX2, OCT4, NANOG and hTERT), ectodermic marker (KRT-18 and NESTIN), endodermic marker (AFP and GATA-4), mesodermic marker (FLT-1, BMP-4 and VE-Cadherin) were used with control primer for β-actin.

Examples 7 and 8

Figure 7:
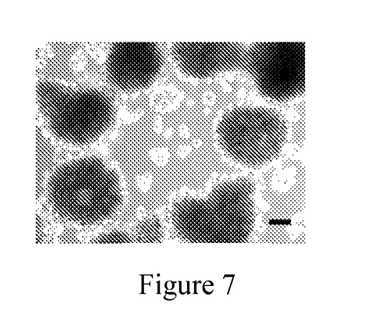
FIG. 7 shows BJ-FiPS formed embryonic bodies (EBs) in suspension culture using AggreWell 800 protocol expression. Bar: 200 μm.
Figure 8:
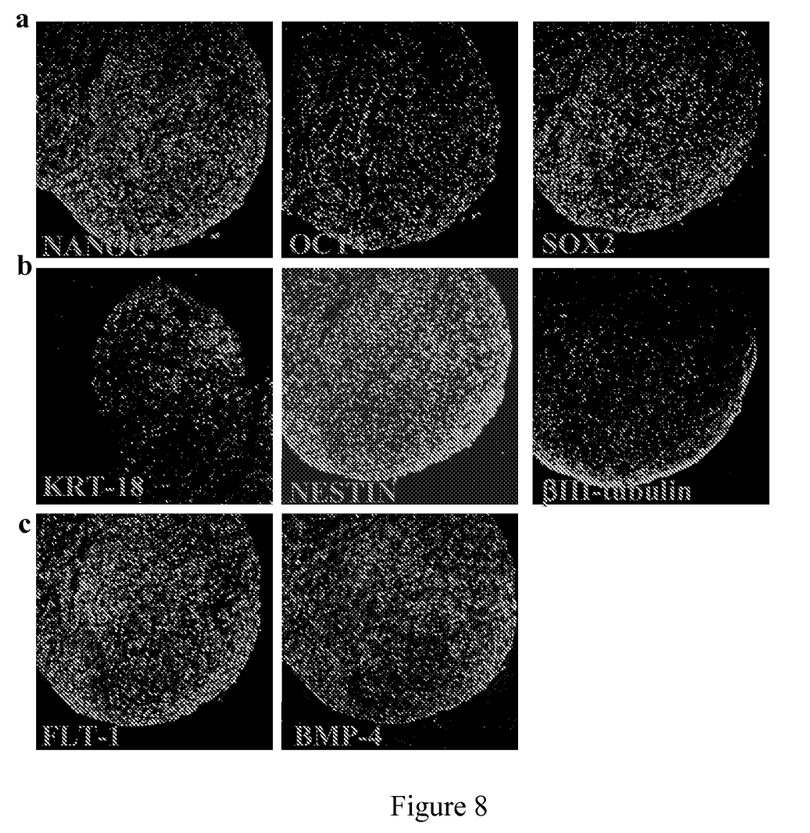
FIGS. 8a-8c show that after 14 days suspension culture, immunostaining revealed that BJ-FiPS EBs expressed with iPS markers (a), as well as ectodermic (b) and mesodermic markers (c).

BJ-FiPS formed embryonic bodies (EBs) in suspension culture using AggreWell 800 protocol (StemCell) (FIG. 7). Furthermore, immunostaining revealed that BJ-FiPS EBs consistently expressed iPS markers such as NANOG, OCT4, and SOX2 as well as ectodermic and mesodermic markers (FIG. 8), which indicated the pluripotency of BJ-FiPS cells.

FIG. 7 shows BJ-FiPS formed embryonic bodies (EBs) in suspension culture using AggreWell 800 protocol expression. Bar: 200 µm.

FIGS. 8a-8c show that after 14 days suspension culture, immunostaining revealed that BJ-FiPS EBs expressed with iPS markers (a), as well as ectodermic (b) and mesodermic markers (c).

Examples 9

For further confirm the pluripotency of BJ-FiPS cells, in vitro differentiation assays were employed. Firstly, BJ-FiPS cells were transferred in α-MEM medium containing 10% fetal bovine serum (FBS), 50 µg/ml ascorbic acid, 10 mM β-glycerophosphate, and $10^{-8}$ M dexamethasone for 21 days. Medium was changed every three days. Alizarin Red S staining revealed that BJ-iPS cells can differentiate to osteoblasts (mesodermic cells) (FIG. 9).

Figure 9:
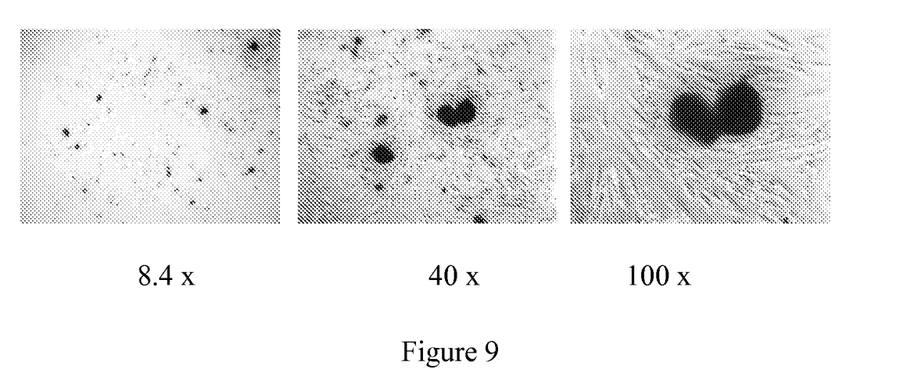
FIG. 9 shows in vitro differentiation of BJ-FiPS cells to osteoblasts.

FIG. 9 shows in vitro differentiation of BJ-FiPS cells to osteoblasts. Bone nodules were stained by Alizarin Red S.

Examples 10-13

Figure 10:
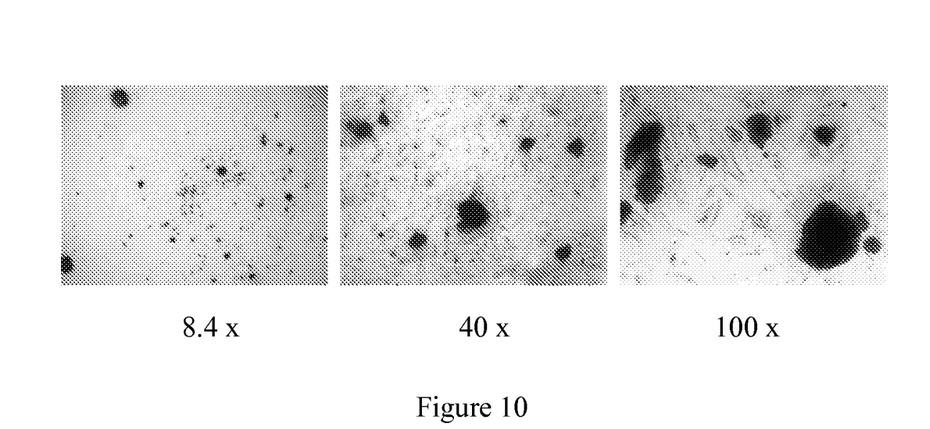
FIG. 10 shows in vitro differentiation of NHDF-FiPS cells to osteoblasts.
Figure 11:
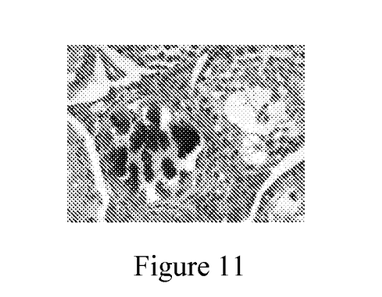
FIG. 11 shows FiPS cells differentiated to bone tissue in SCID-mice testicles.

Similar in vitro differentiation was confirmed with FiPS cells induced from NHDF cells (NDHF-FiPS) (FIG. 10). Furthermore, when injected into the testicles of SCID-mice, FiPS cells differentiated to bone tissue in vivo (FIG. 11). In addition, FiPS cells can differentiate to adipocytes and cardiomyocytes, both are mesodermic cells (FIGS. 12-13).

FIG. 10 shows in vitro differentiation of NHDF-FiPS cells to osteoblasts. Bone nodules were stained by Alizarin Red S.

FIG. 11 shows FiPS cells differentiated to bone tissue in SCID-mice testicles.

Figure 12:
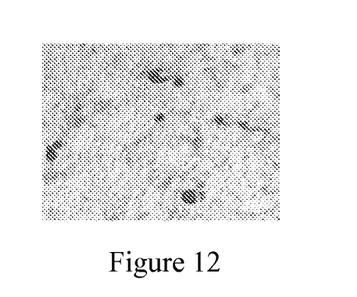
FIG. 12 show FiPS cells were transferred in adipogenesis medium (Lonza) for 21 days.
Figure 13:
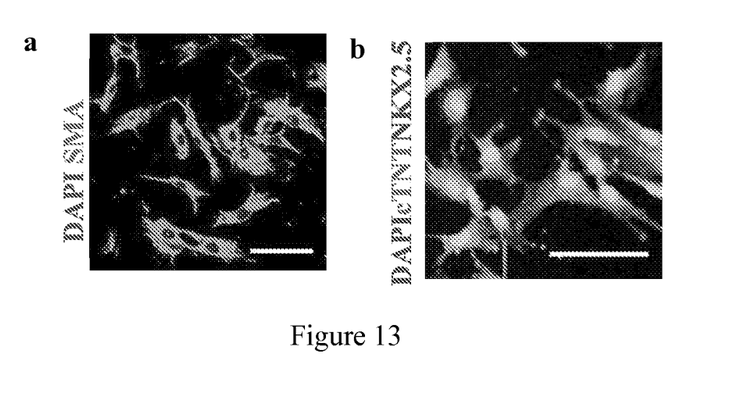
FIGS. 13a and 13b show results of tests on BJ-FiPS cells.

FIG. 12 show FiPS cells were transferred in adipogenesis medium (Lonza) for 21 days. Medium was changed every three days. Oil Red staining revealed BJ-iPS cells can differentiate to adipocytes in vitro.

FIGS. 13a and 13b show FIG. 13. BJ-FiPS cells were transferred in DMEM/F12 (1:1) medium supplied with 20% FBS, 1 mM glutamine, 0.1 mM non-essential amino acid and 0.1 mM 2-mercaptoethanol (EB20 medium) for 4 days suspension culture to form EBs. Then, EBs cells were transferred onto gelatin-coated plates for another 10 days culture for in vitro cardiomyocytes differentiation. Cardimyocytes were characterized by immunostaining of smooth muscle actin (SMA) (a), cardiac troponin (cTNT) and transcription factor NKX2.5 (b). Nuclei were counter stained with DAPI. Bar: 100 μm.

Examples 14-15

Figures 14A, 14B:
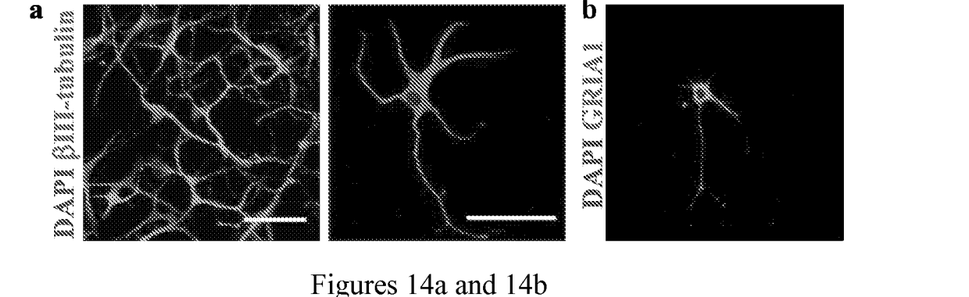
FIGS. 14a and 14b show results of experiments on BJ-FiPS EBS cells.
Figures 15A, 15B:
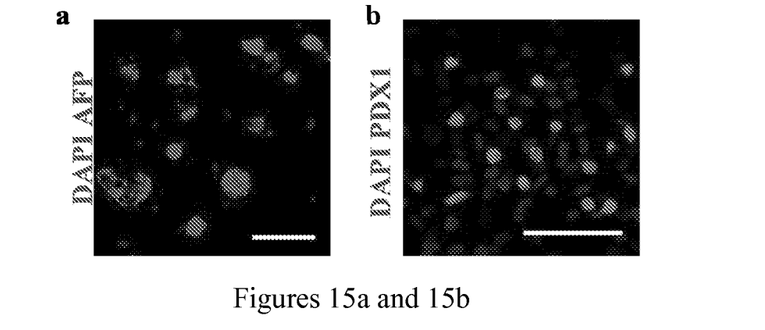
FIGS. 15a and 15b show results of experiments on BJ-FiPS cells growth on feeder cells.

Examples 14 and 15 show that not only FiPS cells are able to differentiate to multiple mesodermic tissue, FiPS cells derived from fibroblasts can also differentiate to ectodermic (FIG. 14) and endodermic cells (FIG. 15).

FIGS. 14a and 14b show BJ-FiPS EBS were suspension cultured in Knockout DMEM medium supplied with 10% Knockout serum, 2 mM glutamine, 10 μM all-trans retinoic acid (RA), and 100 nM of the N-terminal active fragment of human sonic hedgehog (Shh) for 8 days. RA was re-supplied daily, and the whole suspension medium was changed every third day. After that, the induced EBs were transferred on poly-ornithine/fibronection coated plates with DMEM/F12 (1:1) medium supplied with N2, GDNF, BDNF, CNTF, B27 and 2% FBS for neuron differentiation. After 3 days, BJ-FiPS differentiated to neuron (ectodermic cells) characterized by immunostaining of βIII-tublulin (a), and glutamate receptor 1 (GRIA1) (b). Nuclei were counter stained with DAPI. Bar: 100 μm.

FIGS. 15a and 15b show BJ-FiPS cells growth on feeder cells differentiated towards endodermic cells after exposure to 100 ng/ml recombinant activin A in RPMI 1640 medium supplied with 2% FBS and 2 mM glutamine for 4 days, characterized by immunostaining of α-fetoprotein (AFP) (a). After that, BJ FiPS culture in RPMI 1640 medium supplied with 2% FBS and 2 mM glutamine without activin A for another 8 days archived in vitro differentiation of pancrease lineage cell characterized by immunostaining of pancrease/duodenum homeobox 1 (PDX1) (b). Nuclei were counter stained with DAPI. Bar: 100 μm.

Therefore, it is clear that FiPS cells exhibit pluripotency. In addition, in vivo assay suggested the FiPS cells will not induce tumor formation (FIG. 11). Thus, induction of iPS cells with exposure to FMOD and its peptide derivatives will be a safer and better method to direct reprogramming of somatic cells.

Although the foregoing invention has been described in some detail by way of illustration and example for purposes of clarity of understanding, it is understood that certain adaptations of the invention are a matter of routine optimization for those skilled in the art, and can be implemented without departing from the spirit of the invention, or the scope of the appended claims.

We claim:

1. A re-conditioned serum-free cell culture medium composition, obtained by a process comprising
    treating a plurality of mammalian cells with a serum-free cell culture medium for a period ranging from a day to a month, wherein the serum-free cell culture medium comprises (1) a plurality of cell culture medium components comprising at least one inorganic salt, at least one amino acid and at least one vitamin; and (2) fibromodulin (FMOD) or a derivative or fragment thereof, wherein the FMOD is in an effective amount to reprogram a mammalian cell to form a pluripotent stem cell like (PSCL) clone;
    changing the serum-free cell culture medium regularly during the period before transferring the treated mammalian cells on feeder cells until one or more pluripotent stem cell like (PSCL) clones form, wherein the one or more PSCL clones are recognized by an antibody against human Oct4A, Sox2, Nanog, SSEA4, TRA-1-60(S), or TRA-1-81 in immunofluorescent staining; and
    removing the one or more PSCL clones and the remaining mammalian cells, thereby obtaining the re-conditioned serum-free cell culture medium.

2. The composition of claim 1, which is included in a pharmaceutical or cosmetic composition.

* * * * *